United States Patent
Benni et al.

(10) Patent No.: US 8,761,851 B2
(45) Date of Patent: Jun. 24, 2014

(54) INDICATORS FOR A SPECTROPHOTOMETRIC SYSTEM

(75) Inventors: Paul B. Benni, Guilford, CT (US); Bo Chen, Guilford, CT (US); Andrew Kersey, Wallingford, CT (US)

(73) Assignee: CAS Medical Systems, Inc., Branford, CT (US)

( * ) Notice: Subject to any disclaimer, the term of this patent is extended or adjusted under 35 U.S.C. 154(b) by 1250 days.

(21) Appl. No.: 12/096,132

(22) PCT Filed: Dec. 6, 2006

(86) PCT No.: PCT/US2006/061678
§ 371 (c)(1),
(2), (4) Date: Jun. 23, 2008

(87) PCT Pub. No.: WO2007/079316
PCT Pub. Date: Jul. 12, 2007

(65) Prior Publication Data
US 2008/0300474 A1    Dec. 4, 2008

Related U.S. Application Data

(60) Provisional application No. 60/742,801, filed on Dec. 6, 2005.

(51) Int. Cl.
*A61B 5/00*    (2006.01)
(52) U.S. Cl.
USPC ............................ 600/323; 600/334; 600/340
(58) Field of Classification Search
USPC ................. 600/322–328, 330–332, 334, 336, 600/339–341
See application file for complete search history.

(56) References Cited

U.S. PATENT DOCUMENTS

| | | |
|---|---|---|
| 4,653,498 A | 3/1987 | New et al. |
| 5,218,962 A | 6/1993 | Mannheimer et al. |
| 5,387,194 A | 2/1995 | Williams et al. |
| 5,873,821 A | 2/1999 | Chance et al. |
| 6,334,065 B1 | 12/2001 | Al-Ali et al. |
| 6,456,862 B2 | 9/2002 | Benni |
| 6,615,065 B1 | 9/2003 | Barrett et al. |
| 7,031,857 B2 | 4/2006 | Tarassenko et al. |

(Continued)

*Primary Examiner* — Max Hindenburg
*Assistant Examiner* — Adam Eiseman
(74) *Attorney, Agent, or Firm* — O'Shea Getz P.C.

(57) ABSTRACT

A near-infrared spectrophotometric system (e.g., a cerebral oximeter) includes a sensor portion and a monitor portion. The monitor portion includes a processor that runs an algorithm which utilizes the amount of detected light to determine the value of the oxygen concentration (e.g., the absolute level of oxygen concentration). The monitor portion also includes a visual display that displays the determined oxygen concentration values in various formats. The monitor portion may also include an audible device (e.g., a speaker), that provides audible indications of the determined oxygen concentration values. Various visual indicators may include, for example, color-coded graphs of the determined oxygenation values to alert the system user, for example, whether one hemisphere of the brain, or one or more regions of the brain, is in danger of adverse and potentially permanent damage. Also, data may be pre-processed by selecting the most clinically concerning sensor value (e.g., the sensor with the lowest value), and displaying only that sensor value and its identification on the display screen. Alternatively, an average value of multiple sensor measurements may be displayed. This reduces screen clutter and increases the speed of interpretation by the system user. Also, all sensor values may be averaged, and the average value displayed. The determined oxygenation values may also be provided in an audible format.

18 Claims, 5 Drawing Sheets

(56) References Cited

U.S. PATENT DOCUMENTS

| | | |
|---|---|---|
| 7,072,071 B2 | 7/2006 | Kujirai et al. |
| 2002/0016536 A1* | 2/2002 | Benni .......................... 600/323 |
| 2002/0042558 A1* | 4/2002 | Mendelson ................... 600/323 |
| 2003/0135087 A1* | 7/2003 | Hickle et al. .................... 600/26 |
| 2004/0206352 A1* | 10/2004 | Conroy, Jr. ............... 128/204.23 |

* cited by examiner

INDICATORS FOR A SPECTROPHOTOMETRIC SYSTEM

Applicant hereby claims priority benefits of PCT Patent Application no. PCT/US06/61678 filed Dec. 6, 2006 which claims priority to U.S. Provisional Patent Application No. 60/742,801 filed Dec. 6, 2005, the disclosure of which is herein incorporated by reference.

This invention was made with Government support under Contract No. 2R44NS45488-01 awarded by the Department of Health & Human Services. The Government has certain rights in the invention.

BACKGROUND OF THE INVENTION

1. Technical Field

This invention relates in general to a spectrophotometric system for non-invasively determining oxygenation levels in human tissue utilizing near-infrared spectrophotometric techniques, and in particular to such a system having various types of indicators which provide the user with information relating to the determined oxygenation levels.

2. Background Information

The molecule that carries oxygen in the blood is hemoglobin. Oxygenated hemoglobin is known as oxyhemoglobin ($HbO_2$) and deoxygenated hemoglobin as deoxyhemoglobin (Hb). Total hemoglobin is the sum of the two states of hemoglobin (Total $Hb=HbO_2+Hb$), and is proportional to relative blood volume changes, provided that the hematocrit or hemoglobin concentration of the blood is unchanged. The mammalian cardiovascular system comprises a blood pumping mechanism (the heart), a blood transportation system (blood vessels), and a blood oxygenation system (the lungs). Blood oxygenated by the lungs passes through the heart and is pumped into the arterial vascular system. Under normal conditions, oxygenated arterial blood comprises primarily oxyhemoglobin. Large arterial blood vessels branch off into smaller branches called arterioles, which profuse throughout biological tissue. The arterioles branch off into capillaries, the smallest blood vessels. In the capillaries, oxygen carried by hemoglobin is transported to the cells in the tissue, resulting in the release of oxygen molecules. Under normal conditions, only a fraction of the oxyhemoglobin molecules give up oxygen to the tissue, depending on the cellular metabolic need. The capillaries combine together into venuoles, the beginning of the venous circulatory system, and the venuoles combine into larger blood vessels called veins. The veins further combine and return to the heart, and venous blood is pumped to the lungs. In the lungs, deoxyhemoglobin collects oxygen thereby becoming oxyhemoglobin again and the circulatory process is repeated.

The amount of oxygen saturation is typically defined as the ratio of oxyhemoglobin to the sum of oxyhemoglobin and deoxyhemoglobin. In the arterial circulatory system under normal conditions, there is a high proportion of $HbO_2$ to Hb, resulting in an arterial oxygen saturation (commonly referred to as $SaO_2\%$) in the range of 95-100%. After delivery of oxygen to tissue via the capillaries, the proportion of $HbO_2$ to Hb decreases such that the measured oxygen saturation of venous blood (commonly referred to as $SvO_2\%$) is typically lower (e.g., 60%).

One common spectrophotometric method known as pulse oximetry determines arterial oxygen saturation of peripheral tissue (e.g., the finger, ear or nose) by monitoring pulsatile optical attenuation changes of detected light induced by pulsatile arterial blood volume changes in the arteriolar vascular system. Pulse oximetry requires pulsatile blood volume changes to make a measurement. Since venous blood is not pulsatile, pulse oximetry cannot provide any information about venous blood. Also, it is difficult to detect arterial pulse within the brain tissue itself by optical non-invasive means, which reduces the usefulness of pulse oximetry techniques in those applications.

Near-infrared spectroscopy (NIRS) is an optical spectrophotometric method that can be used to continuously monitor tissue oxygenation levels without use of pulsatile blood volume changes. The NIRS method is based on the principle that light in the near-infrared range (700-1000 nm) can pass easily through skin, bone and other tissues where it encounters hemoglobin located mainly within micro-circulation passages; e.g., capillaries, arterioles, and venuoles. Hemoglobin exposed to light in the near-infrared range has specific absorption spectra that vary depending on its oxygenation state; i.e., oxyhemoglobin and deoxyhemoglobin each act as a distinct chromophore. By using light sources that transmit near-infrared light at specific different wavelengths, and by measuring changes in transmitted or reflected light attenuation, concentration changes of the oxyhemoglobin and deoxyhemoglobin can be monitored. The ability to continually monitor cerebral oxygenation levels, for example, is particularly valuable for those patients subject to a condition in which oxygenation levels in the brain may be compromised, leading to brain damage or death.

NIRS-type sensors typically include at least one light source and one or more light detectors for detecting reflected or transmitted light. The light signal is created and sensed in a part of an overall NIRS system that includes a monitor portion having a computer or processor that runs an algorithm for processing signals and the data contained therein. Typically the monitor portion is separate from the sensor portion. As such, the sensor and monitor portions comprise the overall NIRS system. Light sources such as light emitting diodes (LEDs) or laser diodes that produce light emissions in the wavelength range of 700-1000 nm are typically used. A photodiode or other light detector is used to detect light reflected from or passed through the tissue being examined. The NIRS system processor cooperates with the light source and detector to create, detect and analyze the signals in terms of their intensity and wave properties. U.S. Pat. Nos. 6,456,862, and 7,072,071, both of which are hereby incorporated by reference in their entirety and are commonly assigned to CAS Medical Systems, Inc., of Branford, Conn., both disclose an NIRS system (e.g., a cerebral oximeter) and a methodology for analyzing the signals within the NIRS system.

It is known that relative changes in the concentrations of $HbO_2$ and Hb can be evaluated using NIRS apparatus which may include a processor programmed to utilize, for example, a variant of the well-known Beer-Lambert Law, which accounts for optical attenuation in a highly scattering medium such as biological tissue. While this approach to determining oxygenation levels has some utility, it is limited somewhat in that the information it provides relates to a change in the level of oxygenation within the tissue. This approach does not provide for the total value or the absolute value of the oxygen saturation within the biological tissue.

It is known to utilize information regarding the relative contributions of venous and arterial blood within tissue examined by NIRS, where such information was either arbitrarily chosen or estimated, or was determined by invasive sampling of the blood as a process independent from the NIRS examination. For example, it has been estimated that NIRS examined brain tissue comprises about 60% to 80% venous blood and about 20% to 40% arterial blood by volume in the microvasculature. Regarding invasive techniques, blood samples from catheters placed in venous drainage sites such as the internal jugular vein, jugular bulb, or sagittal sinus have been used to evaluate NIRS measurements. However, the estimation technique and the invasive technique have obvious drawbacks, primarily relating to accuracy and to the invasive nature, respectively.

A distinct improvement over these prior art techniques for determining the level of oxygen saturation is the NIRS method and apparatus described and illustrated in the aforementioned U.S. Pat. Nos. 6,456,862 and 7,072,071. U.S. Pat. No. 6,456,862 describes an apparatus and a method for determining the total blood oxygen saturation within tissue. U.S. Pat. No. 7,072,071 also describes an apparatus and a method for determining absolute values of blood oxygen saturation within tissue.

It is further known in the prior art to use comparative spectroscopy methods, such as those described and illustrated in U.S. Pat. Nos. 6,615,065 and 5,873,821. Such methods typically utilize NIRS systems having two or more sensors located, for example, on the human head to access brain tissue with infrared light to thereby determine the oxygenation levels within the brain tissue. However, drawbacks with these comparative spectroscopy methods typically include the need to compare an oxygenation measurement of one region or hemisphere of the brain to oxygenation measurements of other regions of the brain to determine adverse physiological changes by differential analysis or by measuring differential changes from a predetermined initial baseline. Further, with comparative spectroscopy a clinician typically must wait for measurements to be different between two or more sensors to determine if a potential risk of brain damage exists. Therefore a particular disadvantage of comparative spectroscopy is that potential brain damage indications may be missed, because measurements from two or more sensors may give a similar value in which a differential value may be near zero.

What is needed is a spectrophotometric system that determines, for example, the total and absolute oxygen saturation levels within certain biological tissue (e.g., the brain) and provides for various types of indicators (e.g., visual and audible) to quickly and accurately convey to the system user information regarding, for example, the total and absolute oxygen saturation levels with respect to the human subject being monitored by the system.

SUMMARY OF THE INVENTION

A near-infrared spectrophotometric system includes a sensor portion and a monitor portion. For example, the system may comprise a cerebral oximeter that continually monitors the oxygen concentration of hemoglobin within brain tissue at certain locations. The sensor portion may include a light source that comprises, for example, a plurality of laser diodes located together. Each laser diode produces an infrared light signal at a particular wavelength at which a known absorption response is produced depending on the amount of oxygen concentration in the hemoglobin. The sensor portion may also include one or more light detectors (e.g., photodiodes). For example, two light detectors may be included—a "near" detector closest to the light source and a "far" detector farther away from the light source. The light detectors sense a portion of the light from the light source after it has traversed the portion of the tissue of interest. The monitor portion includes a processor that runs an algorithm which utilizes the amount of detected light to determine the value of the oxygen concentration (e.g., the total or absolute level of oxygen concentration, or the change in the level of oxygen concentration) in the tissue of interest. The monitor portion also includes a visual display (e.g., a computer monitor screen, a dedicated CRT display, a flat panel display, etc.) which displays the determined oxygen concentration values and associated information in various formats. The monitor portion may also include an audible device, such as a speaker, for providing audible indications of the determined oxygen concentration values and of the associated information.

The spectrophotometric system may also include a pulse oximeter portion that determines arterial oxygen saturation which, in turn, may be used to determine the venous oxygen saturation. This way, a non-invasive method of distinguishing between blood oxygen saturation within tissue that is attributable to venous blood and that which is attributable to arterial blood is provided.

The processor may make a number of subsequent determinations with respect to the determined values of tissue oxygen saturation. For example, the processor may make a threshold determination in an independent manner from, e.g., the determined absolute tissue oxygen saturation value, where a value below a predetermined threshold may indicate that the brain tissue under examination is in danger of adverse and potentially permanent damage. This threshold determination may be indicated in various ways to the system user (e.g., a clinician).

Diffuse optical tomography may be utilized to visually convey information to the system user regarding the determined tissue oxygen saturation values. For example, two or more system sensors, or an array of light sources and detectors attached to the head, are used together with the processor to determine whether one hemisphere of the brain, or one or more regions of the brain, is in danger of adverse and potentially permanent damage.

Various visual indicators may be provided with the spectrophotometric system for display on the visual display provided as part of the system. The visual indicators may include, for example, graphs of the determined oxygenation values versus time, or the aforementioned diffuse optical tomography visual presentation. The tissue oxygenation values (e.g., the absolute tissue oxygen saturation values) may be color coded, or multiple values may be individually and independently color coded, or a two- or three-dimensional diffuse optical tomography image, with regions color coded, may be provided to indicate and alert the system user, for example, whether one hemisphere of the brain, or one or more regions of the brain, is in danger of adverse and potentially permanent damage. In addition, relatively simplified display indicators for multiple-sensor monitor systems may be provided. For example, data may be pre-processed by selecting the most clinically concerning sensor value (e.g., the sensor with the lowest value), and displaying only that sensor value and its identification on the display screen. This reduces screen clutter and increases the speed of interpretation by the system user. Also, the data may be pre-processed by averaging all sensor values, and displaying the average value on the display screen, again to reduce screen clutter and speed up interpretation. Further, the pulse oximetry measured arterial oxygen saturation value may be displayed on the same display screen as the NIRS tissue oxygen saturation parameters, to thereby simultaneously provide the system user with arterial, tissue and venous oxygen saturation information.

In addition, the determined oxygenation values may be provided to the system user in an audible format. For example, when the spectrophotometric system (e.g., cerebral oximeter) is utilized in conjunction with a pulse oximeter, a series of audible signals may convey information such as pulse rate, arterial oxygen saturation, brain tissue oxygen saturation, and brain venous oxygen saturation. The oxygen saturation values may be audibly conveyed by having a pitch decrease proportional to decreasing oxygen saturation. Since brain tissue oxygen saturation and brain venous oxygen saturation have normal physiological values lower than pulse oximetry arterial oxygen saturation values, the same pitch in tone could be used to indicate normal values. Each oxygen saturation parameter may generate a separate tone with a cardiac pulse resulting from pulse oximetry detection, for example, "beep, beep" for two parameters and "beep, beep, beep" for three parameters, where the pitch may decrease for each tone as the respective oxygen saturation values decrease below normal values. Audible signals may also be used to identify physiologic values from a particular region. If, for example, the system is set to visually display an average of the oxygen saturation values from all of the sensors, audible signals from the sensors can also be employed to give the user additional information regarding the oxygen saturation level and/or change in level, within the one or more regions associated with the sensors. For example, if an average oxygen saturation value is visually displayed in an application where a first sensor is used to monitor the left hemisphere of the patient's brain and a second sensor is used to monitor the right hemisphere, first and second audible signals having particular tones could be utilized to indicate the particular oxygen saturation level in the left and right hemispheres. In the event the oxygen saturation changes in the right hemisphere, for example, the second audible would change in tone to indicate the change and thereby provide the user with useful information. Alternatively, if the system is set to visually display the oxygen saturation value from one or more sensors, audible signals could be utilized to indicate the oxygenation values from those sensors visually and/or not visually represented.

A dynamic safe threshold value may be provided for various tissue oxygen saturation values (e.g., those of the brain). Here, data may be pre-processed with outside subject physiological data, for example, the core body and brain temperature of the human subject under test, to adjust the lower or upper safe threshold to account for physiological changes that may impact the clinical significance in the level of brain tissue oxygen saturation.

These and other objects, features, and advantages of the present invention will become apparent in light of the detailed description of the invention provided below and the accompanying drawings.

DETAILED DESCRIPTION THE INVENTION

Figure 1:
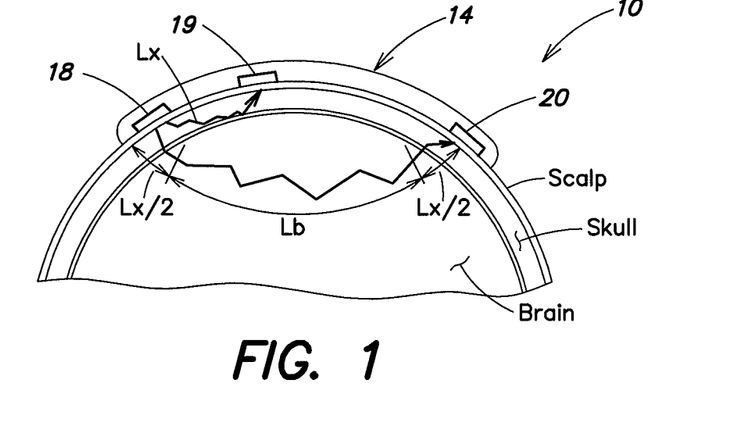
FIG. 1 is a diagrammatic representation of a sensor portion of a spectrophotometric system.
Figure 2:
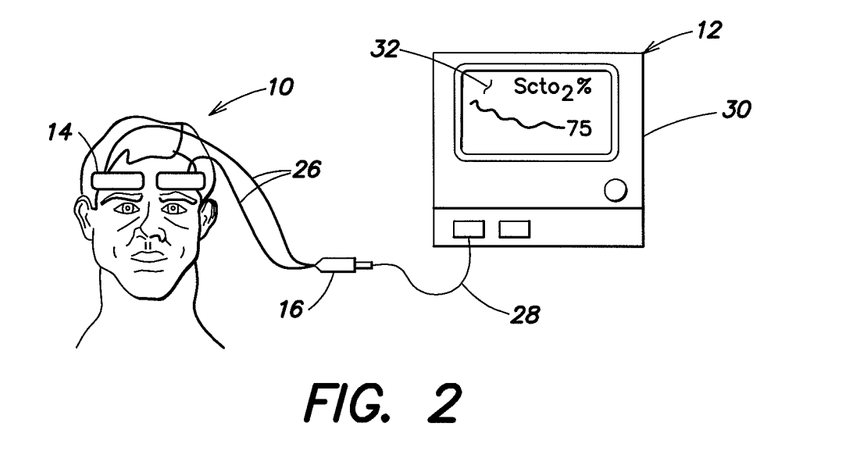
FIG. 2 is a diagrammatic representation of the system of FIG. 1 including an assembly housing or sensor placed on the head of a human subject under test.
Figure 3:
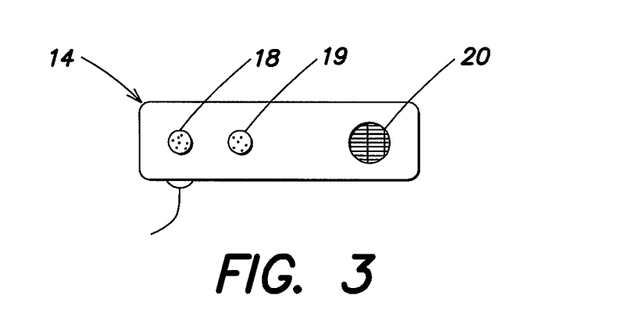
FIG. 3 is a diagrammatic view of a portion of the sensor of FIGS. 1 and 2.

Referring to FIGS. 1-3, a spectrophotometric system may be similar to that described and illustrated in the aforementioned U.S. Pat. No. 7,072,071, which provides for determined absolute values of tissue oxygen saturation. However, the spectrophotometric system described herein is not limited to use with any particular type of oxygenation information. For example, it may be used with absolute tissue oxygen saturation, such as those determined by the aforementioned U.S. Pat. No. 6,456,862, or with determined relative changes in oxygen concentration. The spectrophotometric system includes a sensor portion 10 and monitor portion 12. The sensor portion 10 includes a pair of sensor assembly housings 14 and a connector housing 16. Each sensor assembly housing 14 is a flexible structure that can be attached directly to a location on the body (e.g., the head) of a human subject. The sensor assembly housing 14 may also be referred to hereinafter for simplicity as the sensor 14. Each sensor assembly housing 14 includes a light source 18 and a pair of light detectors 19, 20. A disposable adhesive envelope or pad may be used for mounting the sensor 14 easily and securely to the skin of the human subject under test. The light source 18 may comprise a plurality of laser diodes that emit light signals at narrow spectral bandwidths at known but different wavelengths (e.g., 780 nm, 805 nm, and 850 nm). The laser diodes may be mounted in the sensor assembly housing 14, or may be located remote from the sensor assembly housing 14 in the connector housing 16 or in the monitor portion 12. If located remote from the sensor assembly housing 14, the light output from the laser diodes may be transported via optical fibers to the sensor assembly housing 14. A first connector cable 26 connects the sensor assembly housing 14 to the connector housing 16, and a second connector cable 28 connects the connector housing 16 to the monitor portion 12. The light detectors 19, 20 may comprise photodiodes mounted in the sensor assembly housing 14. The photodiodes may be connected to the monitor portion 12 via the first and second connector cables 26, 28. The monitor portion 12 may, for example, include a computer terminal 30 having an internal computer processor for processing light intensity signals from the light detectors 19, 20 in accordance with various algorithms. The terminal 30 may include a display screen 32 for visually displaying various types of information (e.g., the determined oxygen concentration values) to the system user. The terminal 30 may also include an audible speaker or other type of audible device to provide the various types of information in audible form to the system user.

One advantage of use of an NIRS system that determines absolute values for tissue oxygen saturation is that prior art comparative spectroscopy methods are no longer required to determine if one or more regions of the brain is in danger of adverse and potentially permanent damage. With the present invention, the absolute value of oxygenation concentration can be evaluated relative to a predetermined threshold, below which adverse conditions may likely exist. Therefore, an absolute value measured from any sensor 14 placed on the human head to examine a particular region or hemisphere of the brain can be interpreted independently, without comparison to measurements from other sensors 14 placed on the head to examine other regions of the brain. This avoids the shortcomings of the prior art comparative spectroscopy methods.

If absolute measurements are made from two or more sensors 14 (e.g., an array attached to the subject's head—diffuse optical tomography), a system user can be alerted either visually and/or audibly to potential adverse conditions in one or more regions, or in one or both brain hemispheres, if one or more of the sensors 14 measures an absolute tissue oxygen saturation value below a predetermined threshold. In prior art comparative spectroscopy methods, a clinician must wait for measurements to be sufficiently different between at least two sensors to determine if potential risk of brain damage exists. Therefore, with comparative spectroscopy methods potential brain damage indications may be missed because differences between measurements are insufficient to trigger an alarm, yet the values may be such that a clinically adverse condition exists.

Predetermined threshold values and their relation to the corresponding determined absolute values of tissue oxygen saturation may be communicated to a system user by visual and/or audible indicators associated with the display screen 32 and/or speaker of the terminal 30. For example, absolute oxygen concentration or saturation levels presented in graphic form (i.e., a graph of the determined level or value versus time) may be color coded. A representative color code scheme may be as follows for determined values of absolute brain tissue oxygen saturation ($SctO_2\%$ or $SnO_2\%$) with respect to certain predetermined threshold values and/or ranges: $SctO_2\%$ in the range of from 60% to 89%=GREEN, chance of brain damage is relatively small; $SctO_2\%$:55% to 59%=YELLOW, chance of brain damage is increased, clinical intervention may need to be considered; $SctO_2\%$:50% to 54%=ORANGE, potential high risk of brain damage, clinical intervention should be considered; $SctO_2\%$:0% to 49%=RED, very high risk of brain damage, immediate attention needed—clinical intervention urgently needed; and for a high $SctO_2\%$ value 90% to 100%, the chance of brain metabolism is low due to existing brain damage or other possible physiological change—clinical review of patient condition may need to be considered—this condition may be represented by a color other than those utilized above. A clinician may also be alerted by an accompanying audible signal or alarm that changes in characteristics such as frequency or pitch to indicate the various values above.

Multiple measurements from different sensors 14 can be displayed in graphic form on the display screen 32 with a corresponding color code scheme similar to that above, as well as in a two- or three-dimensional diffuse optical tomography image, with different regions of the brain examined being color coded, to indicate and alert the clinician whether one hemisphere, or one or more regions of the brain is in danger of adverse and potentially permanent damage. In multiple absolute measurements, a clinician can be alerted by an audible signal or alarm that changes in characteristics such as frequency or pitch to indicate if any absolute measurement crosses or goes below a predetermined threshold. Once alerted, the clinician can examine the display screen 32 to determine which region of the brain is at potential risk due to a relatively low tissue oxygenation level.

In a clinical setting where a spectrophotometric system is used to measure and determine tissue oxygen saturation in multiple body positions, it is desirable that the resulting information be displayed in a relatively simplistic and uncluttered manner on the display screen 32. This is done to facilitate relatively rapid interpretation by the system user if clinically adverse events are occurring. To reduce clutter on the display screen 32, the data received from the multiple sensors 14 may be pre-processed and prioritized so that only data from the most clinically significant individual sensor reading is displayed on the display screen 32. For example, the system user may be principally concerned with the sensor 14 that measures the lowest brain oxygenation value, and thus may prefer to be alerted of the low value and which sensor 14 is responsible therefor. If a clinically relevant threshold value is established, the display screen 32 can alert the user of the identification of any sensor 14 that measures a value below the predetermined threshold. This may occur often during decreases in brain oxygenation, since brain hypoxia or ischemia is usually global when cardiac or respiratory problems occur. Conversely, a stroke may affect one hemisphere or region of the brain, where one or more sensors 14 will detect a decrease in brain oxygenation. If the user is alerted, then the information displayed on the display screen 32 can be manually or automatically changed to that corresponding to the sensor receiving the most clinically significant data.

To further reduce display screen clutter, data received from multiple sensors 14 may be pre-processed, by averaging all sensor values and displaying the average value on the display screen 32. If a clinically relevant threshold is established, the display screen 32 can also alert the user of the identification of any sensor 14 that measures a value below the predetermined threshold, along with the pre-processed average value of all sensors 14. Further, these two display methods may be combined. For example, from predetermined priority rules, the average of all sensors 14 can be displayed until the difference in values between sensors 14 exceeds a predetermined value, then the sensor 14 measuring the lowest value along with its identification can be displayed. Thus, the present invention allows for the display of absolute values of brain oxygenation levels relating to the most relevant brain region or hemisphere, where these absolute values or an average thereof may be compared to a threshold or range. Further, in contrast to prior art comparative spectroscopy methods and devices, similarly or equally decreasing values from two or more sensors 14 will be sensed, a problematic situation will be determined, and an indication of such will be provided to the system user. Prior art comparative techniques which compare the values from one sensor to those of another are not likely to flag a scenario wherein both sensor values are similar to one another, but both are indicative of a clinically adverse oxygenation level.

A relatively more complete assessment of regional brain oxygenation may be provided to the system user by having the value of arterial oxygen saturation as measured by a pulse oximetry method, and cerebral oximetry oxygen saturation parameters as measured by the cerebral oximetry method on the same display screen 32. This type of display provides the system user with information regarding arterial, tissue, and venous oxygen saturation levels. These parameters may be displayed on the display screen 32 in numerical and/or graphical form. From these parameters, the system user may determine the arterial-venous oxygen saturation difference and determine the metabolic state of the monitored biological tissue or organ of interest, such as the brain. The arterial-venous oxygen saturation difference may also be displayed on the display screen 32.

Through use of the audible device, such as the speaker within the terminal 30, the clinical relevance of the oxygen saturation levels can be conveyed audibly to the system user, either alone or in conjunction with their visual display on the display screen 32. For example, the oxygen concentration or saturation levels may comprise the combination of pulse oximetry arterial oxygen saturation ($SpO_2\%$) and/or brain tissue oxygen saturation ($SctO_2\%$) from cerebral oximetry, and/or brain tissue venous oxygen saturation ($SvO_2\%$) from cerebral oximetry. An advantage of this aspect of the invention is that the human ear is particularly sensitive to both changes in frequency of sequential sound signal and tonal variations in sequential sound signals. A simple pattern of beating signals can provide the system user with a relatively more complete description of oxygenation status of human subjects without having to first look at the display screen 32. Thus, the audible signals can separately alert caretakers in the immediate vicinity of the system as to the status or level of the different oxygen saturation parameters. The oxygen saturation values may be audibly conveyed, for example, by having a pitch decrease proportional to decreasing oxygen saturation. A single declining pitch tone scale may be used for each unique saturation value with each parameter creating a tone related to its saturation value. Also, since brain tissue oxygen saturation and brain venous oxygen saturation have normal physiological values lower than pulse oximetry arterial oxygen saturation values, the same pitch in tone may be used to indicate normal values for each parameter with the pitch declining from the normal level for each parameter. Each oxygen saturation parameter may generate a separate tone as part of a short sequence of "beeps" or similar tones repeating with every cardiac pulse plethysmographic waveform from pulse oximetry detection. For example, "beep, beep" for two parameters ($SpO_2\%$ and $SctO_2\%$ or $SpO_2\%$ and $SvO_2\%$, respectively), and "beep, beep, beep" for all three parameters. The pitch may decrease for each beep as the respective oxygen saturation values decrease below normal values. This way, if for example $SctO_2\%$ is decreasing while $SpO_2\%$ remains the same, only the pitch of the second beep will be decreasing while the first beep ($SpO_2\%$) will remain unchanged. This change in the difference in audio tones will alert caretakers that brain tissue oxygen saturation is decreasing while the arterial level remains constant, which may lead to a different course of action than if both parameters were declining at the same rate. In this configuration, the beep pitch for $SpO_2\%$, $SctO_2\%$, and $SvO_2\%$ will be the same for their respective clinically normal values (e.g., 100%, 75%, and 65%, respectively). For values of $SctO_2\%$ and $SvO_2\%$ higher than normal, either a higher than normal beep pitch may be used, or the same beep pitch as normal conditions may be used. Alternatively, if pulse oximetry is not available (which typically is the case in cardiac bypass surgeries), a cerebral oximeter may provide an audible beep following the scheme described above to indicate $SctO_2\%$ every fixed period of time to supply audible feedback to the system user when no pulse is present. This audible tone may be of a periodicity and duration so that it is not confused with a regular pulse tone. Also, if an ECG (electrocardiogram) monitor is available, the captured cardiac pulses from the QRS complex may be used to set the frequency of the $SctO_2\%$ or the $SvO_2\%$ beeps to also convey heart rate.

A challenge for establishing proper threshold $SctO_2$ values is that in cardiac and aortic surgeries, mild (32° C.-35° C.), moderate (25° C.-28° C.), or deep (12° C.-15° C.) hypothermia is typically used to cool the patient in an effort to protect the brain by reducing brain metabolism. It is likely that safe threshold $SctO_2$ values differ for various levels of hypothermia, based on a leftward shift in the known oxygen-hemoglobin dissociation curve in which the relation between $SctO_2$ and microcirculatory $pO_2$ (partial pressure of oxygen in blood) changes. A higher threshold $SctO_2$ value may be indicated to maintain a desirable microcirculatory $pO_2$ during brain hypothermia. Therefore, the safe clinical threshold of $SctO_2$ may be adjusted to compensate for physiological changes during hypothermia. This can be accomplished by first determining $SctO_2$ and reading the patient's core body/brain temperature, and then using a predetermined relationship to dynamically change a low safe threshold for $SctO_2$ for a given subject core body temperature. Audible alarm indicators may be utilized to alert the clinician if $SctO_2$ drops below the temperature dependent safe $SctO_2$ threshold.

An example of use of the present invention is described with respect to thoracic aortic surgery. Such surgery often requires that blood flow to the brain be interrupted during the aortic repair. To prevent global cerebral ischemic injury, a state of deep hypothermia is induced via cardiopulmonary bypass (CPB) prior to initiating circulatory arrest. Due to the high rate of cerebral injury during these extreme manipulations, brain protection is a primary concern. In a relevant study carried out, there was no alteration of the surgical procedure or routine clinical monitoring. Patients undergoing elective thoracic aortic surgery were monitored intraoperatively using a cerebral oximeter. Two cerebral oximetry sensors were placed on the subject's forehead bilaterally for continuous monitoring of cerebral tissue oxygen saturation $SctO_2$ in both cerebral hemispheres. In a typical pattern of cerebral oximetry measured cerebral oxygen saturation $SctO_2$ during surgery of aorta, the following events were marked: post anesthesia induction; on cardio-pulmonary bypass (CPB); hard core body cooling to 12° C.-15° C.; deep hypothermic circulatory arrest (DHCA); selective cerebral perfusion (SCP); warming Phase; and off CPB. Nine subjects were monitored. Initial $SctO_2$ readings post induction of anesthesia were 57%-80% (average/SD 68.3±6.3%), which is comparable to healthy awake subjects, whereas $SctO_2$ in room air ranged from 66.6%-79.7% (average 73.6±3.2%), except that in 2 of 9 cases, the $SctO_2$ values were lower than 66% (57% and 61%). During deep hypothermia when the subject is cooled to 12° C.-15° C., it was observed that $SCtO_2$ values increased in most subjects above 80% (⅞ subjects), and in some cases above 90% (⅔ subjects), while in two subjects, the change was minimal, with the maximum $SctO_2$ value between 75%-80%. A rise in $SctO_2$ is expected because deep hypothermia protects the brain by reducing brain metabolism. Furthermore, hypothermia causes a shift of the oxygen-hemoglobin dissociation curve to the left so that for a given $pO_2$, $SctO_2$ is higher, resulting in the observed $SctO_2$ being greater than 80%. Other physiological changes in cerebral circulation may also occur during hypothermia such as arterial to venous shunting, which can affect $SctO_2$ measurements. During DHCA where all blood flow to the brain is stopped for 20 to 30 minutes, the $SctO_2$ decreases to an average value of 62.4±7.0% (range of from 50% to 71%), then increases when cerebral circulation is resumed during SCP.

The significance of the foregoing study is that a cerebral oximeter can make brain oxygen measurements during absence of cerebral perfusion, while other vital sign monitors cannot (during CPB and DHCA, pulse oximetry fails due to lack of arterial pulse; during DHCA, invasive jugular bulb oximetry reading becomes stagnant due to lack of cerebral blood flow.). The clinicians have no guidelines on brain status except for the time duration of circulatory arrest. Another potentially significant observation is that no matter what the peak $SctO_2$ value pre-DHCA, the decrease of $SctO_2$ tends to be the same. For example, in one subject, the peak $SctO_2$ value was 92%, the lowest value at the end of DHCA was 70%; and for another subject, the peak $SctO_2$ value was 78%, the resultant lowest value at the end of DHCA was 56%, which may prove to be below a safe $SctO_2$ threshold during deep hypothermia. Initial analysis of the relationship between $SctO_2$ values and patients' core temperature indicates that for the two patients who have low peak $SctO_2$ values, cooling of the patient's brain might be less optimized. It is possible that the initiation of DHCA was too early for the patient's brain to be cooled thoroughly.

Figure 4:
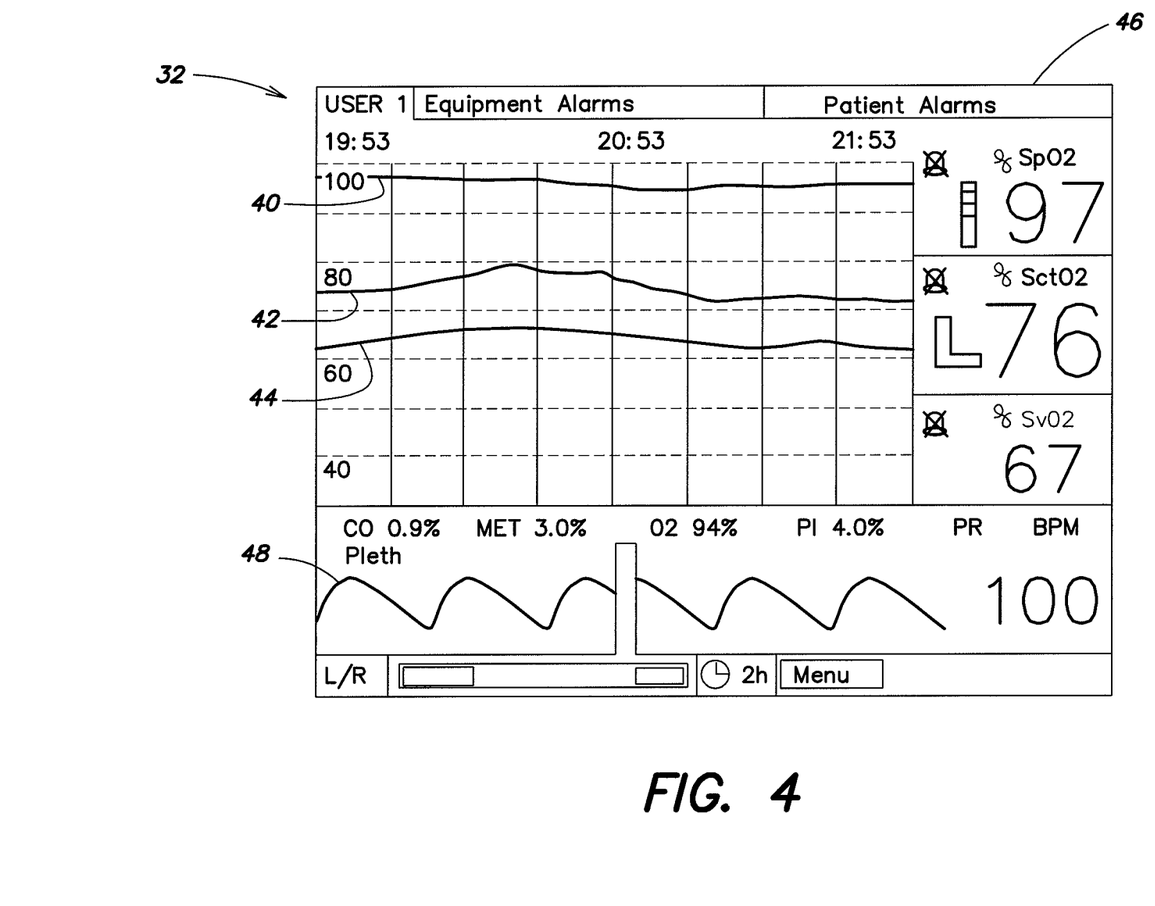
FIGS. 4-7 are diagrammatic representations of display screens of the system of FIG. 2 for displaying various information to the system user.
Figure 5:
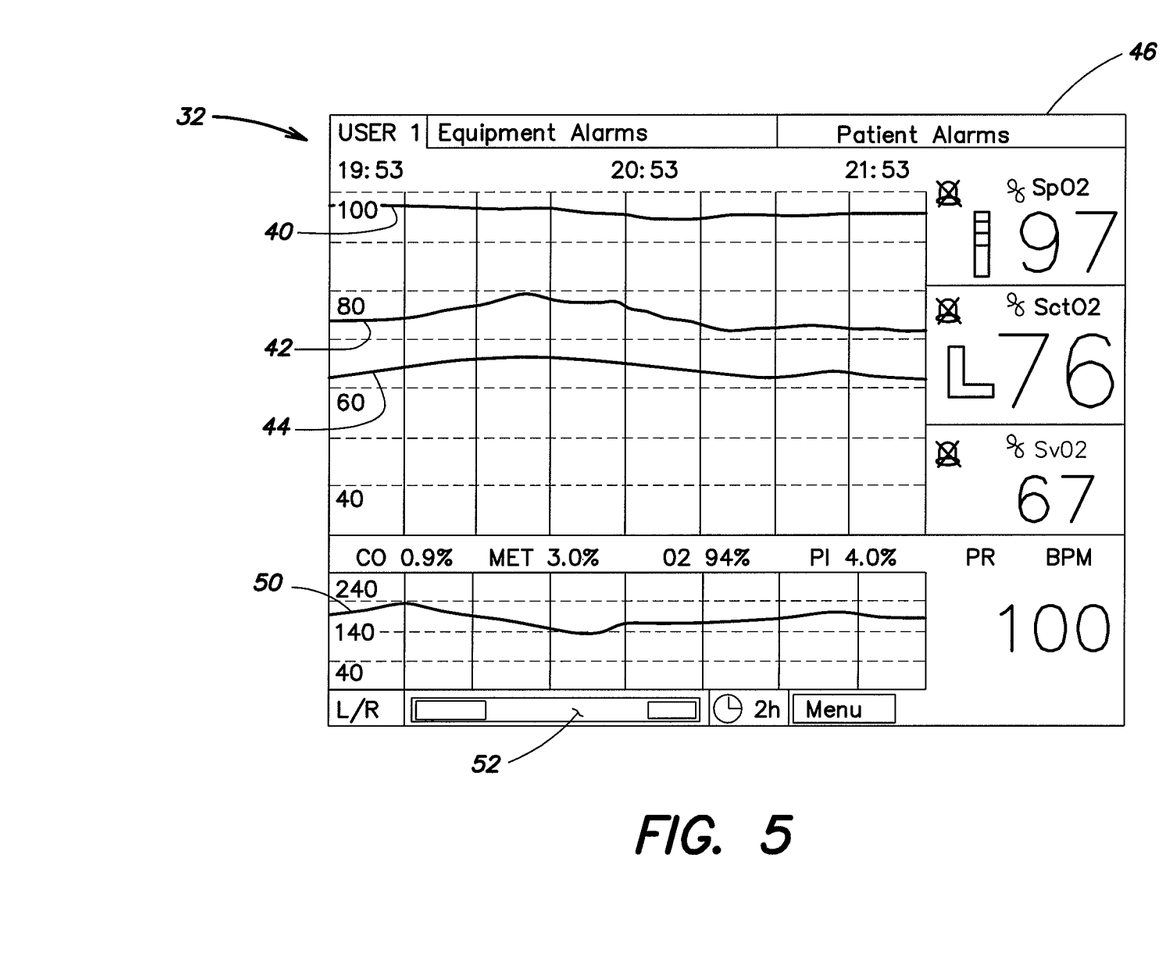
Figure 6:
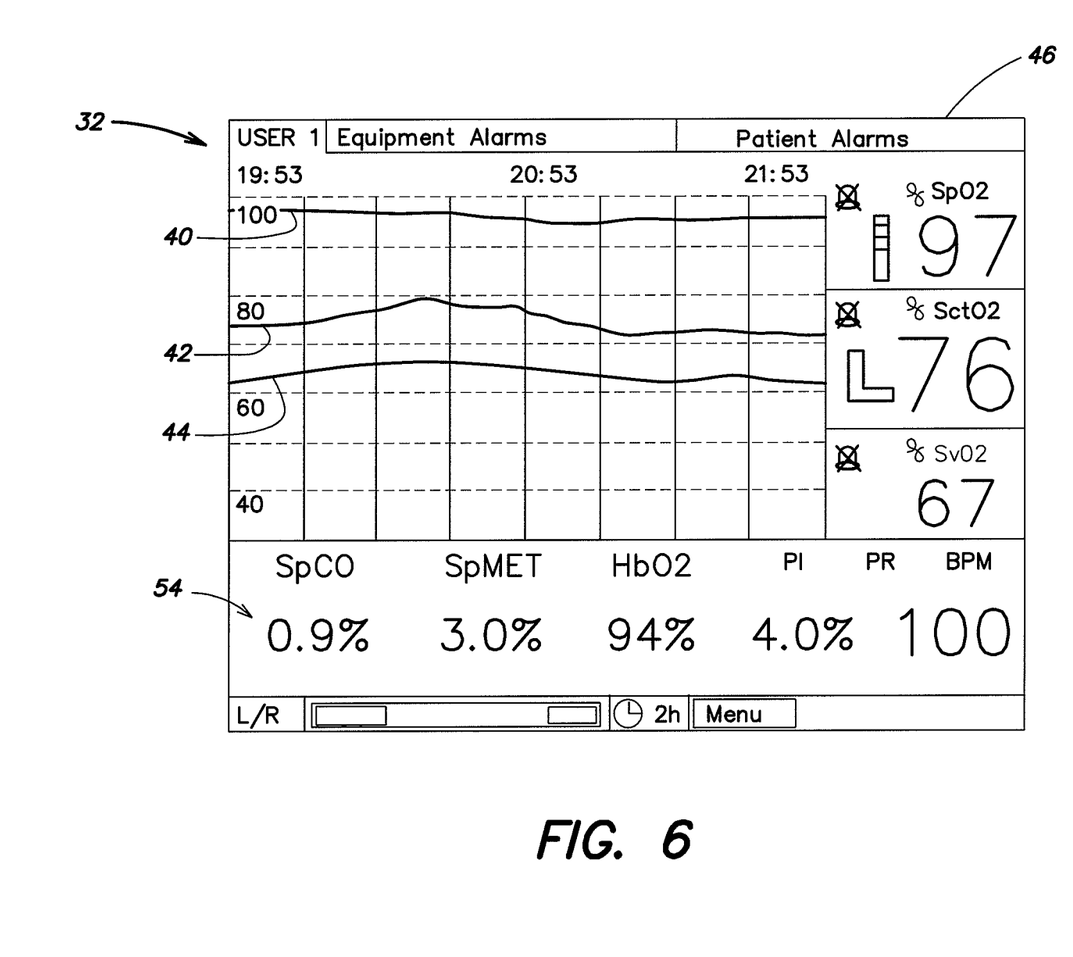
Figure 7:
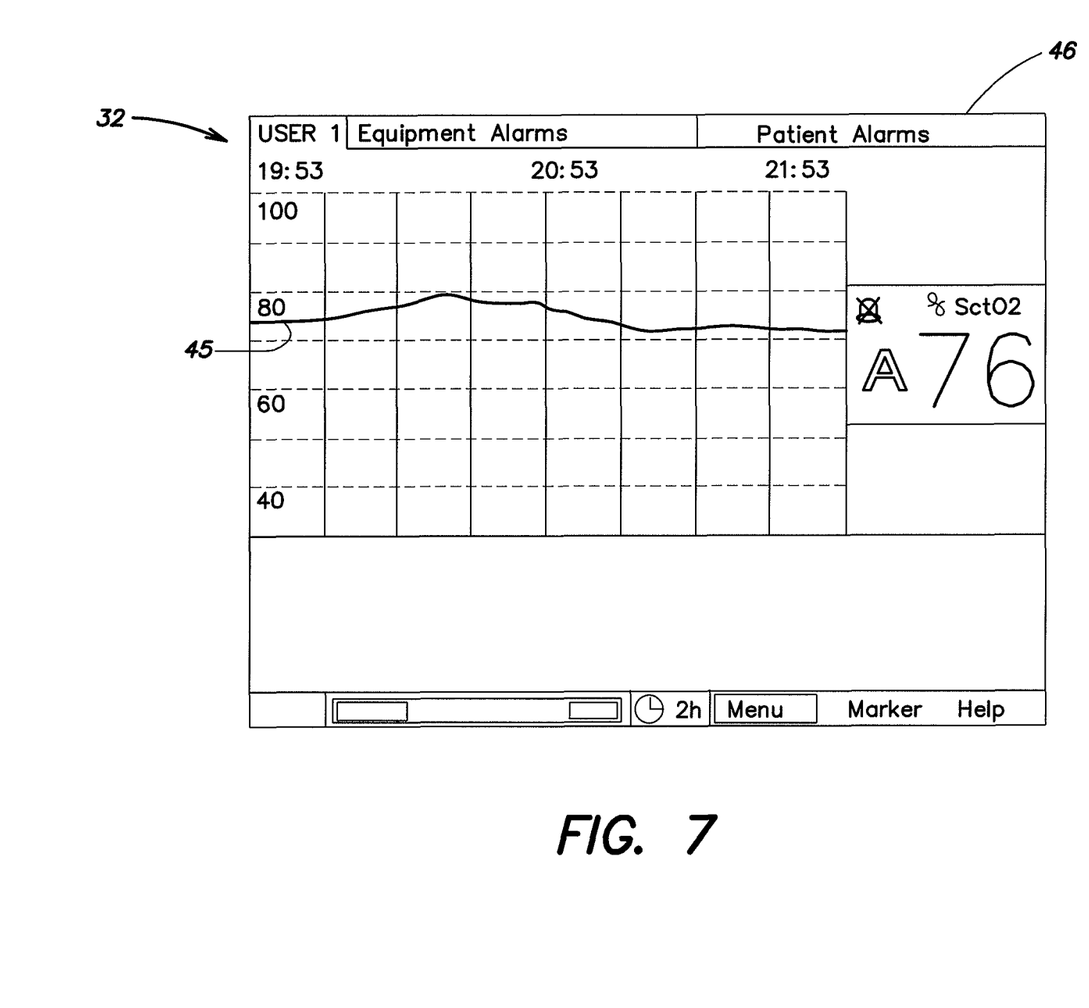

Referring to FIGS. 4-7, there illustrated are various representative visual screens of information that are shown on the display screen 32 of the terminal 30. The visual screens provide the system user with information relating to the various measured and determined oxygenation parameters. FIGS. 4-6 each illustrate a graph portion of the visual display that includes three curves 40-44. The top curve 40 indicates the determined value for percentage oxygen saturation (% $SpO_2$) versus time over a two hour period (e.g., from time=19:53 until time=21:53), as determined by pulse oximetry techniques associated with the system. The time period of the data displayed may be other than a two hour period, if desired. The middle curve 42 indicates the determined value for percentage brain tissue oxygen saturation (% SctO$_2$) versus time for the same two hour time period, while the lower curve 44 indicates the determined value for percentage venous blood oxygen saturation (% SvO$_2$) versus time for the same two hour time period. The boxes to the right of each curve 40-44 indicate the then-current real-time numeric value for each parameter, while the letter "L" indicates that values displayed are for the left sensor 14 of the two sensors 14 attached to the head of the human subject (FIG. 2). The system user may also view the data associated with the right sensor 14, if desired, indicated by the letter "R". If an average value for the multiple sensors is selected, then the letter "A" or "Ave" may be indicated next to the value (see FIG. 7). The bell symbol with an "X" therethrough in each box indicates that the audible alarm associated with a limit warning for that particular parameter has been turned off. The system user may, if desired, turn the audible alarm on. The rectangular image displayed in the % SpO$_2$ box is a vertical plethysmograph that indicates pulsatile changes associated with that parameter. The system user may, if desired, view data from other time periods than that shown. Also, the system user may view other types of information associated with the parameters, such as the average value of a parameter or parameters over a certain period of time. In FIGS. 4-6, the "Patient Alarms" indicator 46 in the top right corner of the display screen may be one or more graphical symbols that will, for example, illuminate or blink to indicate a limit violation of a parameter. The data information displayed in a horizontal line below the lower curve 44 (e.g., "CO 0.9%," "MET 3.0%," etc.) illustrate the values of various data parameters associated with a pulse oximeter attached to the human subject under test. Such data is typically collected for a finger or ear lobe mounted sensor, and does not represent data collected from the left or right sensors 14. FIG. 7 illustrates a visual display that includes a graph portion having a curve 45 that represents the average oxygen saturation value of the data collected by the sensors. The letter "A" in the box to the right of the curve indicates that an average value is being displayed.

In FIG. 4, below the pulse oximeter data is shown a plethysmograph 48 ("Pleth"), which represents data collected from the pulse oximeter related to % SpO$_2$ and is a different visualization of the data shown by the plethysmograph image shown in the % SpO$_2$ box. The vertical bar travels across the screen to refresh the plethysmograph data. The numeral "100" to the right of the Pleth 48 represents the numeric pulse rate of the human subject. As discussed above, this data is collected typically from a pulse oximeter sensor mounted on a finger or ear lobe, and does not represent data collected from a left or right head-mounted sensor 14. The format of the Pleth display may be constant regardless of time scale or scrolling selection.

In FIG. 5, below the pulse oximeter data instead of the plethysmograph 48 is located a pulse rate graph 50 with the same time scale as the three curves 40-44 above. The data used to generate the pulse rate graph 50 is provided by the pulse oximeter. The format of the pulse rate display area may change with both time scale and scrolling selections. The times at the top of the screen also reflect the data displayed in the pulse rate area. If a two hour time scale is selected, the pulse rate data will represent two hours. Changing the scrolling bar 52 will display the associated pulse rate data for that time (similar to the curves 40-44).

In FIG. 6, located below the three curves 40-44 instead of the plethysmograph 48 of FIG. 4 or the pulse rate graph 50 of FIG. 5 is a horizontal display 54 in large numerals of the additional parameters (SpCO, SpMET, HbO$_2$, PI, and PR) provided by the pulse oximeter. The system is versatile in that the system user can select which of the formats for displaying information as in FIGS. 4-6.

Although the invention has been illustrated and described with respect to several preferred embodiments thereof, various changes, omissions and additions to the form and detail thereof, may be made therein, without departing from the spirit and scope of the invention.

What is claimed is:

1. A method for non-invasively determining the blood oxygen saturation level within a subject's tissue, using a spectrophotometric system that includes a processor, a visual display, and a plurality of sensors, each sensor having at least one light source operable to transmit a light signal into the subject's tissue, and at least one light detector operable to sense the light signal after passage through the subject's tissue and to produce signal data representative of the sensed light signal, the method comprising the steps of:
   positioning the sensors relative to the subject to sense separate regions of the subject;
   sensing the subject's tissue and determining an absolute oxygen saturation level for each region using sensed signal data from each region;
   displaying the oxygen saturation level for a selected region, or an average of the oxygen saturation levels of all of the regions, on the visual display;
   comparing the absolute oxygen saturation level of each region to a predetermined value that is based on established data, and which predetermined value is an absolute value independent of oxygen saturation values determined from the subject's tissue, and determining if the absolute oxygen saturation level of each region represents an adverse condition relative to the predetermined value;
   replacing the oxygen saturation value of the selected region or average value then currently displayed with the absolute oxygen saturation value of the region having the most adverse oxygen saturation value relative to the other regions.

2. The method of claim 1, wherein the predetermined value represents a minimum oxygen saturation value, and the adverse condition represents an oxygen saturation value below the minimum oxygen saturation value.

3. The method of claim 1, wherein the step of displaying the oxygen saturation level includes displaying one or more colors, where each color is associated with a level of oxygen saturation.

4. The method of claim 3, wherein a first color represents a first range of oxygen saturation values, a second color represents a second range of oxygen saturation values, and a third color represents a third range of oxygen saturation values, wherein the first, second, and third ranges are independent of one another, and each color is distinguishable from the other colors.

5. The method of claim 1, further comprising the step of adjusting the predetermined value in relation to one or more physiological parameters of the subject.

6. The method of claim 5, wherein the physiological parameters include the subject's temperature.

7. The method of claim 1, further comprising the step of providing an audible indicator of the oxygen saturation level for the region being displayed.

8. The method of claim 7, wherein the audible indicator changes as the oxygen saturation level changes.

9. The method of claim 7, wherein the audible indicator changes in pitch or frequency.

10. The method of claim 1, further comprising the step of providing an audible signal indicating that the display of the oxygen saturation level has changed from the selected region or average, to the region having the most adverse condition.

11. The method of claim 1, further comprising the step of providing an audible signal indicative of the oxygen saturation level for one or more of the regions having an oxygen saturation level not visually displayed.

12. The method of claim 1, further comprising an audible signal indicative of the subject's pulse or arterial oxygen saturation level.

13. The method of claim 1, further comprising an audible signal indicative of the subject's venous oxygen saturation level of a particular region or average venous oxygen saturation level.

14. A method for non-invasively determining the blood oxygen saturation level within a subject's tissue, using a spectrophotometric system that includes a processor, a visual display, and a plurality of sensors, the method comprising the steps of:
  positioning the sensors relative to the subject to sense separate regions of the subject;
  sensing the subject's tissue and determining an absolute oxygen saturation level for each region using signal data produced from each region;
  providing a predetermined value for comparison with the absolute oxygen saturation level of each region, which predetermined value is based on established data, and which predetermined value varies depending on a temperature of the subject;
  comparing the absolute oxygen saturation level of each region to a predetermined value, and determining if the absolute oxygen saturation level of each region represents an adverse condition relative to the predetermined value; and
  selectively displaying the absolute oxygen saturation level for one or more regions on the visual display.

15. The method of claim 14, wherein the region displayed has the most adverse oxygen saturation value relative to the other regions.

16. The method of claim 14, wherein an average of the oxygen saturation levels for the regions is displayed.

17. The method of claim 16, further comprising the step of replacing the oxygen saturation value of the region or average value then currently displayed with the oxygen saturation value of the region having the most adverse oxygen saturation value relative to the other regions.

18. A method for non-invasively determining the blood oxygen saturation level within a subject's tissue, using a spectrophotometric system that includes a processor, a visual display, and a plurality of sensors, the method comprising the steps of:
  positioning the sensors relative to the subject to sense separate regions of the subject;
  spectrophotometrically sensing the subject's tissue and determining an absolute oxygen saturation level for each region using sensed signal data from each region;
  displaying the absolute oxygen saturation level for a selected region, or an average of the absolute oxygen saturation levels of all of the regions, on the visual display;
  comparing the absolute oxygen saturation level of the regions relative to each other, selecting a maximum absolute oxygen saturation value and a minimum absolute oxygen saturation value, and determining a difference between the maximum and minimum values; and
  comparing the difference to a predetermined value, and if the difference exceeds the predetermined value, replacing the absolute oxygen saturation value of the selected region or average value then currently displayed with the minimum absolute oxygen saturation value.

* * * * *